ional Patent [19]

Burnhill

[11] Patent Number: 4,922,928
[45] Date of Patent: May 8, 1990

[54] VAGINAL DEVICE
[76] Inventor: Michael Burnhill, 269 Lafayette Ave., Chatham, N.J. 07928
[21] Appl. No.: 232,951
[22] Filed: Aug. 17, 1988
[51] Int. Cl.⁵ .............................................. A61F 13/20
[52] U.S. Cl. .................... 128/832; 128/834; 604/286; 604/369
[58] Field of Search ............... 128/833, 830, 832, 834, 128/838; 604/11, 15, 55, 28 G, 369, 904

[56] References Cited
U.S. PATENT DOCUMENTS

| | | | |
|---|---|---|---|
| 732,855 | 7/1903 | Hewish | 604/286 |
| 3,128,762 | 4/1964 | Young | 128/834 |
| 3,916,898 | 11/1975 | Robinson | 604/286 X |
| 4,198,976 | 4/1980 | Drobish et al. | 128/832 |
| 4,200,090 | 4/1980 | Drobish | 128/832 |
| 4,219,016 | 8/1980 | Drobish et al. | 128/832 |
| 4,274,410 | 6/1981 | Chvapil | 604/11 X |
| 4,393,871 | 7/1983 | Vorhauer et al. | 128/833 |
| 4,424,054 | 1/1984 | Conn et al. | 604/11 |
| 4,564,362 | 1/1986 | Burnhill | 604/286 |
| 4,693,705 | 9/1987 | Gero | 604/286 X |

*Primary Examiner*—Randolph A. Reese
*Assistant Examiner*—Jeffrey L. Thompson
*Attorney, Agent, or Firm*—Evelyn M. Sommer

[57] ABSTRACT

A three layered disposable vaginal device comprised of two resilient compressible polymeric foam layers separated by a non-permeable layer, the outermost layer being designed to include a receptacle. The device is also designed to include a removal tape that will permit the user to easily remove the same after use. The construction is intended for use as a barrier contraceptive with or without spermicide, as a delivery system for medicaments and also as a barrier to the transmission of sexually transmitted diseases.

25 Claims, 1 Drawing Sheet

VAGINAL DEVICE

This invention relates to a vaginal device and more particularly relates to a vaginal sponge used as a barrier contraceptive, as a barrier to disease transmission, as a carrier for a contraceptive or as a carrier and dispenser of medicaments, such as anti-infectives, anti-virals, anti-inflammatories, anti-fungals, hormones, enzymes, psychotropic drugs and the like.

More particularly, the invention relates to a disposable female contraceptive and/or a vaginal medication device adapted for insertion and placement in the human vaginal canal and subsequent removal therefrom for the local administration of a spermicide or one or more of a variety of medicaments.

The invention also relates to a barrier contraceptive device which is relatively inexpensive, affords a very high degree of protection from pregnancy and disease transmission and overcomes some of the problems and disadvantages associated with other contraceptive devices and methods which will be described below.

It is abundantly clear that one of the most crucial problems of man is the expanding population. Already the large cities are experiencing a disconcerting modern symptom of being "people trapped." What is more, the Malthusian nightmare of population exceeding the food supply has become a reality. Major efforts have been directed to thwart this crisis. The development of the oral contraceptive—i.e., the "pill" has been hailed as one of the major discoveries of our age and more significant to the human race than the release of atomic energy or space flights.

Unfortunately, there are side effects and certain risks involved in the taking of oral contraceptives. From 15 to 35% of the women using the oral contraceptives experience undesirable side effects. Nausea, vomiting, breast fullness, mastalgia, headache, dizziness, depression, apathy, fatigue, pelvic pain and chloasma are the most frequent. Fluid retention and weight gain are also observed. Thrombophlebitis has been the cause of greatest concern to the profession, the FDA and the public. Instances of jaundice have been reported. There has been some indication that contraceptive therapy may increase the blood pressure in a segment of the patients. Concerns have been raised about a possible relationship with cervical cancer, breast cancer and liver cancer.

There are other contraceptive products available. They vary in mode of application, time of application, nature of device, cost, adverse affects and reliability. For the purpose of this disclosure, there may be mentioned the diaphragm, IUD's, the cervical cap, foams, jellies, suppositories and the vaginal sponge as described in U.S. Pat. No. 4,393,871.

The diaphragm and cervical cap involve the intervention of a physician and are expensive and in the case of the cervical cap may produce discomfort, infection and other problems. They are also difficult to sterilize and messy to clean.

Recently increasing attention has been given to the adverse reactions caused by intrauterine devices (IUD's). Both the scientific and the lay presses have reported the occurrence of serious side effects associated with their use, including pelvic inflammatory disease, ectopic pregnancy, and impaired fertility after discontinuing use. The foams, jellies and suppositories do not require a physician, are inexpensive and have the disadvantages that they are unpleasant and/or messy to use, frequently cause irritation to the user and/or her partner, and have reliabilities of 85% or less.

It has already been proposed (U.S. Pat. No. 3,262,450) to use as a birth control method foam producing spermicidal compositions which are topically applied with a cellular sponge of polyurethane plastic in which the average pore size does not exceed 1.5 mm. A foam producing material is introduced into the device which is termed "a topical application." Just prior to use the foam is produced by compressing and expanding the sponge and then this foam filled application is introduced into the vaginal cavity. Such structure possesses several deficiencies, including the already mentioned messiness of foams and more important that the applicator can not retain the spermicide containing foam any great length of time and thus has limited long term applicability.

A vaginal sponge contraceptive has been disclosed in U.S. Pat. No. 3,762,414 issued in 1973 to the inventor named herein. This sponge is a compressible, smooth surfaced, plastic sponge in the form of a solid rectangle, cylinder, sphere or the like and as disclosed is divided into two or more sections by a plastic, latex or other rubber sheet or film. The dividing sheet or film prevents the flow of fluid from one section of the sponge to the other. The sponge is used for controlling the flow of seminal fluid (contraception) and for dispensing medicaments.

The use of the aforesaid sponge as a contraceptive is enhanced by incorporating into the sponge a spermicidal agent as, for example, a copper salt. Still further, the sponge as described in the patent may be used as a carrier and dispenser for medicaments, for example, as are used to treat infections.

As disclosed in U.S. Pat. No. 3,762,414, the vaginal sponge is produced from polyurethane foam or other smooth surfaced plastic foam and is divided into at least two sections separated by a plastic latex or other non-porous fluid impervious film. The contraceptive action is provided by sponge-like absorption of sperm by the foam material and blockage of the passage of such sperm by the film used to separate the sponge sections. Contraception is enhanced by the use of a chemical contraceptive which is absorbed and released in a sponge-like controlled manner.

Recently a non-prescription sponge contraceptive has been disclosed (V.L.I. Corporation of Costa Mesa, Calif. U.S. Pat. No. 4,393,871) which is round in shape and which is adapted to release a chemical, NONOXYNOL-9, generically known as nonylphenoxy poly(ethyleneoxy)ethanol that inactivates sperm. The V.L.I. sponge contraceptive is formed by foaming a contraceptive surfactant and a foam forming polymeric material or a monomer or prepolymer thereof. According to V.L.I. the polymerized foam substantially encapsulates the contraceptive surfactant so that the same will be slowly released for use only in those cases where the surfactant is present in large enough amounts i.e., greater than 10% of the dry weight of the sponge. If present in an amount less than 10% of the dry weight of the sponge, an organic fibril such as collagen must be added to help encapsulate the contraceptive agent.

This sponge, as in the case of the device disclosed in U.S. Pat. No. 3,762,414, also blocks the cervix and also acts to trap and absorb semen. As described by the press, "in clinical trials, the sponge was found to be about 85% effective in preventing pregnancy."

In addition to causing some discomfort to the user, the shape and location in the vaginal canal have given rise to removal problems.

In U.S. Pat. Nos. 4,564,362 and 4,601,714 barrier contraceptives have been disclosed which comprise an outermost layer of a resilient compressible open-celled polymeric foam, a non-porous barrier film layer affixed to the outermost foam layer and a second layer of open-celled polymeric foam affixed to the opposite surface of the non-porous film layer. The outermost and innermost foam layers differ in density and/or number of pores per inch with the more dense or smaller pored foam layer constituting the outermost layer, the outermost layer being adapted to lie against the cervix of the uterus.

The device itself constitutes a barrier contraceptive, the contraceptive action being provided by sponge-like absorption of sperm by the foam and blockage of the passage of such sperm by suitable selection of the foam and by the film used to separate the outermost and innermost sponge layers. The effectiveness of the device is enhanced by the introduction of a chemical contraceptive into at least one of the sponge layers, preferably during the manufacturing process for retention therein and from which it is absorbed and released in a sponge-like controlled manner. The presence of the spermicide serves to improve the device's effectiveness as a contraceptive.

When the device is used as an article for controllably dispensing drugs, the same or different drugs can be introduced into at least one of the sponge layers. These drugs may be adapted for rapid release or for release over a prolonged period of time. The device permits the retention and therewith timed release application of medicaments or drugs.

The incredible increase in the incidence of sexually transmitted diseases during the last decade has drastically changed the need for devices to be used during coitus. The emphasis in the last quarter century has been to improve the efficacy, safety and acceptability of contraceptives and has resulted as aforenoted, in the development of oral contraceptives, intrauterine contraceptive devices, the use of hormonal implants and injections and as well of simplified forms of both male and female sterilization. The unanticipated and unexpected emergence of virally transmitted sex associated diseases such as the group of human papilloma viral diseases, herpetic lesions and human immunodeficiency viral disease has drastically altered the requirements for safe and efficacious aids to protect not only against pregnancy but against sexually transmitted disease. These diseases have required that consideration be given not only to contraceptive efficacy, but additionally to offer means of protecting sexual participants from acquiring diseases that may in many instances be incurable, if not fatal.

It is an object of the present invention to provide a multi-purpose vaginal device suitable for use in contraception and medicament application improved as compared to the state of the art with respect to consumer acceptance, efficacy and production feasibility.

A further object of the invention is to provide a multi-purpose vaginal device that completely prevents fluid flow from one of its ends to the other and yet is porous and absorbent.

Still a further object of the present invention is to provide a vaginal contraceptive device having an improved effectiveness in preventing pregnancy.

Yet a further object of the invention is to provide a vaginal device of the type described which may be economically mass produced and which may be simply packaged to facilitate storage and transportation thereof prior to use.

Another object of the invention is to provide a vaginal device of the type described for controllably dispensing drugs.

Yet another object of the invention is to provide a vaginal device of the type described for providing protection from disease transmission.

Another important object of the invention is to provide a vaginal device having an improved effectiveness in preventing pregnancy and additionally providing protection against the transmission of any sexually transmitted disease.

Still another object of the invention is to provide a vaginal device of the type described in which access is provided to the device for easy removal thereof.

These and further objects and advantages of the invention will be made clear or will become apparent during the course of the following description.

In accordance with the present invention, a vaginal device is provided the outermost layer of which is a polymeric foam. Affixed to the outermost foam layer is a non-porous film layer made of a liquid, virus and bacteria proof soft elastomeric material. Affixed to the non-porous film layer is a second layer of polymeric foam. The intermediate layer provides a barrier between the two foam layers. The outermost layer is formed so as to provide a receptacle therein for spermicide and/or medicament. The presence of the receptacle also adapts the device for use as a collector of menstrual fluid and discharges. The presence of the receptacle in the outermost foam layer allows the device to naturally orient itself over the cervix increasing the blocking action of the device and also permits deeper placement in the vagina decreasing interference during coitus. Further the presence of the receptacle makes insertion and removal easier than in the case of a uniformly dense continuous outermost layer.

In the drawings which form an integral part of the specification and are to be read in conjunction therewith, and in which like parts are designated by the numerals in the various views.

Figure 3:
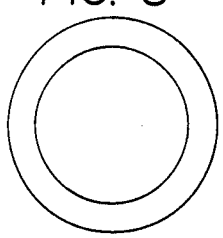
FIG. 3 is a top view of the vaginal device of the invention.

The device as constructed is a three dimensional structure, cylindrical in shape and forms a more or less circular unit having a diameter of about 40 to 75 mm and a depth of about 25 to 75 mm. The invention is not limited to the foregoing dimensions, the same being illustrative only. Its diameter may decrease somewhat but this aspect is limited as it is critical that the device form a barrier across the vaginal canal. The innermost and outermost layers should have a thickness of from 10 to 20 and 15 to 55 mm respectively. Such thicknesses insure ready impermeability, yet also provide flexibility. The receptacle provided in the outermost layer may be spherical or globular in shape or may take the form of a truncated cone. Its diameter at its topmost aspect should be about 20 to 45 mm and it should have a depth of 5 to 50 mm. It is critical that the size of the receptacle be regulated so as not to interfere with the dimensional stability and/or structural integrity of the device but yet provide ample space for spermicide, medicament and/or collected fluid.

The barrier film should have a thickness of about 0.5 to about 3 mils, preferably from 1 to 2 mils.

As noted hereinabove, the device in use must be positionable to block the cervical opening and for making a compression seal against the walls of the vaginal canal.

The foam must of course be biocompatible, non-toxic and non-irritating and is preferably a polyurethane foam. In addition the foam must be natural and soft in feeling so that the user in the case of medical application and in the case of contraceptive use, the latter including barrier use for preventing the acquisition of a sexually transmitted disease, neither sexual partner is aware of its presence. Any polyurethane foam which can be fabricated with the characteristics needed for the intended end use (soft, pliable, flexible, porous, may be employed.

While the polyurethane foams are preferable, there are not presently any reasons why the polyester, polyether, polyethylene, crosslinked polyethylene and the like combination foams, as for example polyester-polyurethane foams may not be used. In addition the alginates, polymeric Hypan compounds, have been found to be suitable for use in the fabrication of the device of the invention. The criteria for selection of course must include in addition to effectiveness, safety for intended use.

Preferably, the foams are open cell, but it would appear that closed cell foams would work as well. It has been found that the closed cell foams are especially suitable for fabricating the outermost layer i.e., layer provided with the receptacle. The cell structure most preferably is open cell, 80–200 pores per inch. The density of the foam will vary as hereinafter described but can range from 1.5 to 3.0 lbs. per cu. ft. and even higher.

The tensile strength characteristics are somewhat important and should amount to about 30–39 psi. It can be appreciated that the foams involved are readily available and that there is no difficulty envisioned should there be a need to custom fabricate so as to produce the desired characteristics.

Most important, the sponge must be permeable, must be capable of absorbing, retaining and then releasing a spermicide or medicament. At the same time, it must be a barrier for the microsized highly motile sperm. In this case, the pore size is critical not only for barrier effectiveness but for ensuring retention of the spermicide or medicinal agent for any appreciable period.

Foams marketed under the trade names Scott Industrial Foam, Scottfelt Foam, Pyrell and the like are particularly suitable for use in producing the device of the invention. Two foams are used in constructing the instant device with the foams being selected so as to provide layers of differing resiliency, stiffness and absorbency. The density and cell structure, particularly the pores per inch, determine the characteristics. In some applications the more dense or smaller pored foam is preferably selected for forming the outermost layer.

The two layers, however, may be the same or different. In the latter case, the foams may have different characteristics of resiliency and absorbency.

The foam layers are separated one from the other by a barrier film. The film barrier can be made of natural rubber, synthetic rubber or latex material, or other elastomeric material. It is also possible to use as a barrier layer certain of the laminated packaging materials, as for example a barrier coextruded layer comprised of a two or three layer combination of ethylene methacrylate copolymer and polyester. It is contemplated that in place of the barrier film a glue layer may be used. As glue there may be used any suitable adhesive i.e., one which is pharmacologically acceptable, biologically inert and capable of forming an impervious layer. An example of such an adhesive layer is a polyolefin adhesive layer. Another adhesive which may be used is ethylene acrylic acid.

The layers of sponge are so arranged as to provide an outermost layer provided with a receptacle and which aids in securing the device, holding the device in position, and which furthermore reinforces the barrier effect of the film and of the innermost sponge layer.

The use of a string or thread or woven fabric ribbon is contemplated for facilitating removal and/or withdrawal of the device, removal tapes being preferred. Alternate removal means may be substituted as for example tab means applied with a biocompatible adhesive on the exposed surface and capable of being grasped and/or held while the device is being removed.

Accordingly, it can be appreciated that the use of the urethane-barrier film or adhesive layer sponge device per se without the addition of a spermicidal agent is contemplated as reliable for contraceptive and disease transmission use.

However, the efficacy is improved when prior to its use as a contraceptive the receptacle provided in the outermost layer is filled with a spermicide, such as NONOXYNOL-9, generically known as nonylphenoxy poly(ethyleneoxy)ethanol which has long been recognized as safe and effective for this purpose. Other examples of spermicides which are suitable for use herein include, methoxypolyoxyethyleneglycol 500 laureate, stearic acid, ricinoleic acid, p-diisobutylphenoxyethoxyethanol, p-menthanylphenylpolyoxyethylene ether, octylcresolpolyoxyethylene ether, polyoxyethylene oxypropylene stearate, polyoxyethylene laureate, glycerol ricinolate, triisopropyl phenylpolyoxyethylene ether, mono-iso-octyl phenyl ether, polyethylene glycol, polyoxyethylene stearylamine, benzalkonium chloride, sodium dodecylsulfate, sodium oleate, zinc phenolsulfonate, dodecylbenzene sulfonate, dodecyl diaminoethyl glycine, and the like.

The spermicide is required to be present in an effective amount and the size of the receptacle is dimensioned so as to provide at least that amount.

No preservatives or pH reducers should be required but if they are added, it is well within the skill of the art to determine in what amounts the same may be present and the manner in which they are to be incorporated into the various formulations prior to their use.

Instances of preservatives include benzoic and sorbic acid.

An example of an agent which may be added to lower the pH is citric acid. The pH in the vagina is approximately 4.0 to 5.0. If the vaginal pH is increased to any extent above this range, the growth of bacteria is encouraged. The citric acid can be added in an amount whereby the pH of the solution in the sponge is below that of the vaginal pH and namely below 4.0 and preferably at about 3.5.

In addition to the spermicide or in place thereof, pharmaceuticals such as antibiotics, antifungals, antivirals, antibacterials, steroids, etc., illustrated hereinafter, can be delivered into the receptacle provided in the sponge.

Thus, and this is most important, the sponge may be used as means for dispensing medicaments as for example, anti-infection agents, anti-microbials, anti-virals, hormones, enzymes, psychotropic drugs, cardiac and blood pressure regulators, etc. This aspect of the invention is considered to be a very important one. Further, the medicament itself or the medicament and sponge may be modified for controlled or timed release during use.

Illustrative of the suitable medicaments and the categories in which they fall are the following:

| Name | Category |
|---|---|
| aminophylline | smooth muscle relaxant |
| aspirin | analgesic |
| conjugated estrogen ethinylestradiol | estrogen |
| prostaglandin | labor inducing |
| iodochlorhydroxyquin | local anti-infective |
| interferon, acyclovir | antiviral |
| metronidazole | anti-trichomonal |
| sulfonamides | antibacterial |
| retin A | anti-dysplasia |
| miconazole | anti-fungal |
| prochlorperazine | tranquilizer |
| ketoconazol | anti-yeast and anti-Candida |
| nystatin | |

Other medicaments which can be mentioned are barbiturates, narcotics, phenobarbital, procaine, penicillin, tetracycline, ampicillin, cephalosporins, nitrofurazone, hydrocortisone, triamcinolone, prostaglandine and the like.

While in one aspect the device of the invention is a vaginal barrier that is designed to afford reasonable contraceptive efficacy, most importantly it serves to provide protection against the transmission and/or acquisition of any sexually transmitted disease. It is now known that the passage of sperm through the cervical canal is one of the ways in which pathogenic microorganisms gain access to the upper genital tract (uterus, fallopian tubes, and ovaries). Several investigators have established, for example through use of such means as electron microphotographs, the adherences of bacteria to the heads and necks of spermatozoas thereby providing for them a piggy back ride to the upper genital tract. Contraceptive methods such as the IUD do not protect women against this route of transmission. Tubal ligation and oral contraceptives also do not appear to provide a reliable means of protecting women against sexually transmitted diseases. The vaginal barrier device of the invention provides three mechanisms that serve to prevent the transmission of disease.

first: an innermost or distal sponge layer to absorb spermatozoa.
second: an impermeable barrier layer to prevent transmission of spermatozoa and microorganisms including viruses.
third: a spermicidal/bactericidal/virucidal agent to immobilize and kill spermatozoa and microorganisms that penetrate beyond the first two defense layers.

The provision of the receptacle in the proximal portion of the device further enhances the efficacy of the device of the invention. It now becomes suitable for the collection of samples of cervical secretions or menstrual fluid. Tissue specimens thus collected may then be evaluated with respect to infertility, hormonal status, or cancer screening. An even more likely use would be for the collection of menstrual fluid to serve as a sanitary system for menstrual protection that might be safer and more comfortable than those currently in use i.e., tampons and napkins.

The device of the invention not only allows for the delivery of medicaments to the vagina or circulatory system but the presence of the receptacle enables it to be used to deliver spermatozoa to the upper vagina and cervix. This delivery capability decreases the loss of spermatozoa during insemination procedures done in infertile or subfertile patients, and increases the amount of contact time of the spermatazoa with the cervix.

The presence of the receptacle also allows for the placement of monitoring devices that can record and transmit information on the temperature, pH, glucose content, and other chemical and mineral constituents of upper vaginal/cervical/uterine fluids that would be of interest and importance in physiological investigations and infertility therapies. These measuring devices would be of particular importance to the prediction and monitoring of ovulation important both in reducing infertility and in using "natural" methods of family planning by enhancing the effectiveness of periodic abstinence.

If the sponge's effectiveness in preventing transmission of disease is to be enhanced, the use of an antiviral agent such as idoxiredome, acyclovir, interferon and the like is particularly indicated.

For using the vaginal device of the present invention to deliver spermicide or to deliver medication including anti-virals to the vagina or the cervix, an effective amount of the spermicide or of the desired drug is incorporated into an appropriate pharmaceutical carrier, for example a cream, foam, gel or the like and in this form introduced into the receptacle portion of the device.

The amount of drug introduced into the receptacle provided in the vaginal device of the present invention varies, depends on the particular drug, the desired therapeutic or prophylactic effect, and the time span for which the device provides therapy. The upper limit and the lower limit will depend on the activity of the drug and the time span of its release from the device. Thus, it is not practical to define a range for the therapeutically effective amount of drug to be incorporated in or released by the vaginal device.

As noted, the above drugs and other drugs can be present in the vaginal device alone or in combination with pharmaceutical carriers to make the drugs more easily delivered and retained in the device. The carrier may also contain adjuvants for preserving, stabilizing, wetting, emulsifying, and the like.

The vaginal sponge of the invention can be fabricated by any of the conventional foam techniques. The incorporation of the film between the two foam layers is known, as are the techniques for making the foams. Any of the known methods of molding, extrusion, stamping, etc., may be used singly or in combination to make the device.

The method of manufacture of the end product polymer sponge must encompass its packaging as it is critical with a product of this type that the product be delivered in a sanitary or sterile form. A number of packaging methods are contemplated including the use of barrier laminates such as are presently used in connection with liquid, food, cosmetic and medical products The sponge is placed on a sheet of barrier film which is thereafter covered over with a further sheet of the same film and sealed on all four sides. If the packaging involves the use of an envelope or bag sealed on three sides or even one side, the respective sides not so sealed can thereafter be sealed using an adhesive if necessary or by relying on the heat seal nature of the barrier film itself. It is contemplated that in place of heat, ultrasound, RF or other form of sealing techniques can be used. The atmosphere, materials and other precautionary measures are observed to provide a sterile packaged sponge. What results is a packet of the type known in the art for retaining a product for prolonged periods of time having a long shelf life, yet easily opened when needed.

Figure 1:
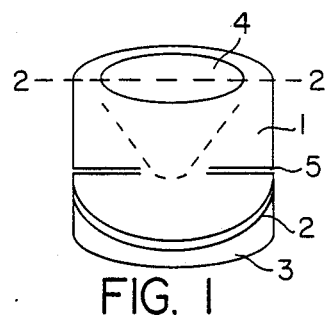
FIG. 1 is a front view of the vaginal device of the invention.

Referring to FIG. 1, an outermost layer 1 of open cell polyurethane foam having about 150 pores per square inch and having a thickness of about 42 mm is affixed to a latex film 2 having a thickness of about 1.5 mils. The innermost layer is an open cell polyurethane foam 3 having about 100 pores per square inch and having a thickness of about 13 mm. The device is a cylindrical construction having a diameter about 60 mm and a thickness just exceeding 55 mm.

Figure 2:
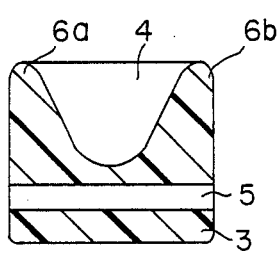
FIG. 2 is a sectional view taken along the line 2—2 in FIG. 1.

As illustrated in FIGS. 2 and 3, the receptacle 4 occupies less than 3/5ths of the device i.e., it has a total depth of about 30 mm, a diameter at its topmost portion of about 40 mm tapering down to about 20 mm at its lowermost portion which is located approximately 12 mm above the base of the outermost layer 1 and the latex film or barrier film layer 2.

Figure 4:
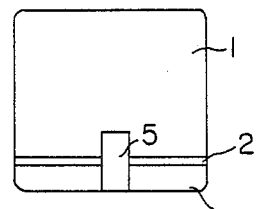
FIG. 4 is a side view showing a removal tape for facilitating removal of the device after use.
Figure 5:
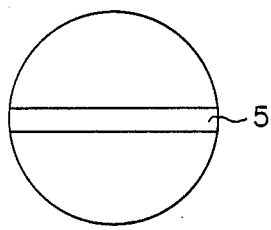
FIG. 5 is a bottom view of the vaginal device of the invention.

As shown in FIGS. 4 and 5, a removal tape 5 is provided for facilitating removal. The tape 5 can be made of a cotton or nylon woven or non-woven material. It can also be made of any other non-irritating material as for example of a synthetic plastic such as polyester, which is soft, non-irritating and biocompatible. In the preferred embodiment, the removal tape has a thickness of 7 mm and is introduced in the manufacturing process for providing retention in the device under the tension exerted thereon in effecting removal. The tape can be continuous or interrupted, extends into the uppermost layer but below the terminating portion of the receptacle. The tape 5 as provided allows the vaginal device to be easily grasped for removal from the vaginal canal. The presence of the receptacle 4 in the uppermost portion of the device contributes to the ease with which the device is inserted and removed. It is readily apparent while the barrier across the vaginal canal is readily retained, the device is particularly well adapted to lie against the cervix of the uterus and the edges 6a and 6b of the outermost layer being adapted to block the vaginal fornices.

While the device constituting my invention has been described as being more or less circular in shape, other shapes, i.e., elliptical, pear and the like, are contemplated.

In the same manner, while the device has been disclosed as consisting of two (2) layers of sponge separated by a layer of impervious film, it is of course possible to have additional layers of sponge. However, at least one layer of impervious film must be present and disposed between two layers of sponge, i.e., only one layer of impervious film is required, regardless of how many foam layers are present.

While it has been indicated that the spermicide, or medicament is introduced into the receptacle for delivery therefrom, it can be appreciated that the device is in the main constituted of a polymeric foam or sponge material and that the sponge material will absorb and retain spermicide or drug so that it too serves as a vehicle for retention and/or dispensing of the spermicide or medicament. In fact the sponge serves to assure that a reserve of spermicide or medicament i.e., antiviral agent is available.

It is also contemplated that a layer of suitable adhesive (pharmacologically acceptable and capable of forming an impervious barrier layer) may be substituted for the elastomeric film.

As noted above, while polymeric foams such as polyurethane are preferred, alginate and polymeric hypan compounds can be used to equal advantage.

It is well within the skill of the artisan and the user as to how the device is to be inserted and removed and accordingly, the details thereof need not be expressly set forth.

It is also believed well within the skill of the art to appreciate how to introduce the spermicide or medicament into the receptacle.

It is contemplated that the spermicide and/or medicament can be provided to the user in a single packet or that they can be provided separately.

It is further contemplated that the outermost layer be constructed of a non-porous material and that in such circumstances, no barrier film layer will be required.

I claim:

1. A vaginal device having a depth of about 25 to 75 mm comprising an outermost layer of a resilient compressible polymeric foam having a depth of from 15 to 55 mm, a non-porous film layer formed of a liquid proof soft material affixed to said outermost layer of polymeric foam and a second innermost layer of resilient compressible polymeric foam affixed to the opposite surface of said nonporous film layer having a depth of from 10 to 20 mm, said outermost layer being foamed so as to provide an open ended receptacle therein terminating within said outermost layer at a distance above said nonporous layer so as to provide three barrier layers said receptacle having a depth of 5 to 50 mm for receiving a spermicidally and/or pharmaceutically effective agent and for adapting said device to naturally insert itself over the cervix.

2. A vaginal device according to claim 1 wherein said device is a three dimensional structure cylindrical in shape.

3. A vaginal device according to claim 1 having a diameter of about 40 to 75 mm.

4. A vaginal device according to claim 1 wherein said receptacle is in the shape of a truncated cone.

5. A vaginal device according to claim 1 wherein said receptacle's diameter at its topmost aspect is 20 to 45 mm.

6. A vaginal device according to claim 1 wherein said barrier film layer has a thickness of from 0.5 to 3 mils.

7. A vaginal device according to claim 1 wherein said foam layers are fabricated of a member selected from the group consisting of polyurethane, polyester, polyether, polyethylene foams, hydrophillic Hypan polymers, alginates and combinations thereof.

8. A vaginal device according to claim 7 wherein said foam is a polyurethane foam.

9. A vaginal device according to claim 7 wherein said foam layers are fabricated of open cell foams.

10. A vaginal device according to claim 7 wherein said foam layers are fabricated of closed cell foams.

11. A vaginal device according to claim 1 wherein said barrier film layer is made of a natural rubber, synthetic rubber or latex material.

12. A vaginal device according to claim 1 wherein said barrier film layer is a glue layer made of a pharmaceutically acceptable adhesive.

13. A vaginal device according to claim 12 wherein said adhesive is a member selected from the group consisting of polyolefin and ethylene acrylic acid adhesives.

14. A vaginal device according to claim 1 provided with means for facilitating removal of the device.

15. A vaginal device according to claim 14, wherein said means is a removal tape.

16. A vaginal device according to claim 14, wherein said means is a removal tab.

17. A method for providing contraception which comprises inserting a vaginal device according to claim 1, into the vagina of a female subject prior to intercourse so that the outermost layer lies against the cervix of the uterus and blocks the vaginal vault.

18. A method according to claim 17 which comprises directly before inserting said device, introducing an effective amount of a spermicide into the receptacle portion thereof.

19. A method for dispensing drugs and other medicaments, which comprises inserting a vaginal device according to claim 1, into the vagina of a female subject requiring treatment with the drug which has directly preceding insertion been introduced into the receptacle portion thereof.

20. A vaginal device according to claim 1 wherein said innermost and outermost foam layers are each fabricated of the same type of foam, said layers being separated one from the other by said nonporous film layer.

21. A method for preventing disease transmission which comprises inserting a vaginal device having a depth of about 25 to 75 mm comprised of an outermost layer of a resilient compressible polymeric foam having a depth of 15 to 55 mm, a non-porous film layer formed of a liquid proof soft material affixed to said outermost layer of polymeric foam and a second innermost layer of resilient compressible polymeric foam affixed to the opposite surface of said non-porous film layer having a depth of from 10 to 20 mm, said outermost layer being formed so as to provide an open ended receptacle therein having a depth of 5 to 50 mm and terminating within said outermost layer at a distance above said nonporous layer so as to provide three barrier layers, into the vagina of a female subject prior to intercourse so that the outermost layer lies against the cervix of the uterus and blocks the upper vaginal vault.

22. A method according to claim 21 which comprises directly before inserting said device, introducing an effective amount of an antiviral agent into the receptacle portion thereof.

23. A vaginal device comprising an outermost layer of a resilient compressible polymeric foam, a nonporous film layer formed of a liquid proof soft material affixed to said outermost layer of polymeric foam and a second innermost layer of resilient compressible polymeric foam affixed to the opposite surface of said nonporous film layer, said outermost layer being formed so as to provide an open ended receptacle therein, said receptacle having a depth which permits termination thereof within said outermost layer and at a distance above said nonporous layer so as to provide three barrier layers.

24. A vaginal device according to claim 23 wherein said device has a thickness of about 55 mm and said receptacle occupies less than 3/5 of said device.

25. A vaginal device according to claim 23 wherein said outermost layer has a thickness of about 42 mm, said latex film has a thickness of about 1.5 mils, said innermost layer has a thickness of about 13 mm, and said receptacle has a total depth of about 30 mm.

* * * * *